United States Patent [19]
Tsao

[11] Patent Number: 5,605,544
[45] Date of Patent: Feb. 25, 1997

[54] SAFETY INJECTOR WITH RETURNABLE NEEDLE

[76] Inventor: Chien-Hua Tsao, 7Fl., No. 6, Lane 134, Sec. 2, Chung Hsiao East Rd., Taipei, Taiwan

[21] Appl. No.: 600,256

[22] Filed: Feb. 12, 1996

[51] Int. Cl.⁶ ............................................. A61M 5/00
[52] U.S. Cl. ................................. 604/110; 604/195
[58] Field of Search ........................... 604/110, 187, 604/192, 195, 263

[56] References Cited

U.S. PATENT DOCUMENTS

| | | | |
|---|---|---|---|
| 5,180,369 | 1/1993 | Dysarz | 604/100 |
| 5,180,370 | 1/1993 | Gillespie | 604/110 |
| 5,221,262 | 6/1993 | Kite | 604/195 X |
| 5,318,536 | 6/1994 | Williams | 604/195 X |

*Primary Examiner*—John D. Yasko
*Attorney, Agent, or Firm*—David & Raymond; Raymond Y. C. Chan

[57] ABSTRACT

A kind of safety injector comprises a drug tube assemblage, an injector needle assemblage and a soft release element. A drug tube assemblage includes an outer tube for storing medicament, a hollow push rod with hollow inner portion for accepting the injector needle, and a rubber plunger which is movable together with the hollow push rod and having a frangible sealing element. The injector needle assemblage includes a body which is connected and attached in replaceable way to the top side of the outer tube, an injector needle with its base which is caught in the body in a releasable way, and an elastic element which exerts downwards elastic force to the needle base. After accomplishing the injection, the hollow push rod is continually pushed upwards for very short distance with the soft release element moving together, and the injector needle with its base is forced to separate from the body by the release element. Furthermore, the elastic element forces the needle base and the needle which is fixed on it to remove downwards. After having destroyed the frangible sealing element of the rubber plunger, on way of its downwards displacement, the injector needle with its base drops into the inner space of the hollow push rod so that the happening of injury by the contaminated needle after injection can be avoided.

12 Claims, 15 Drawing Sheets

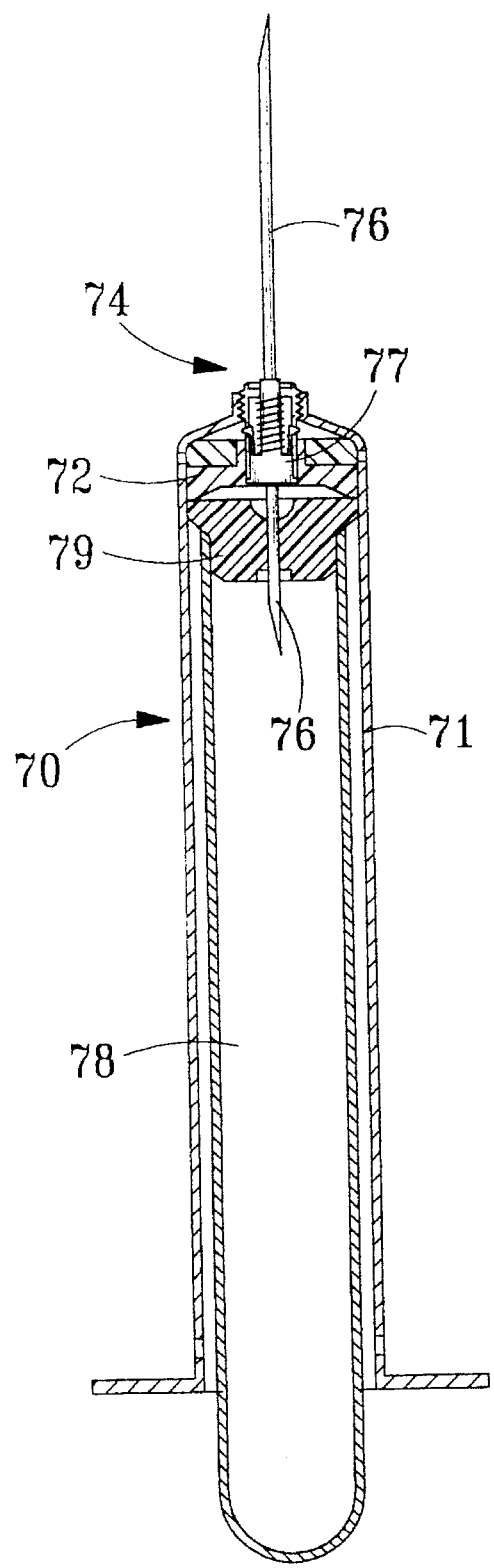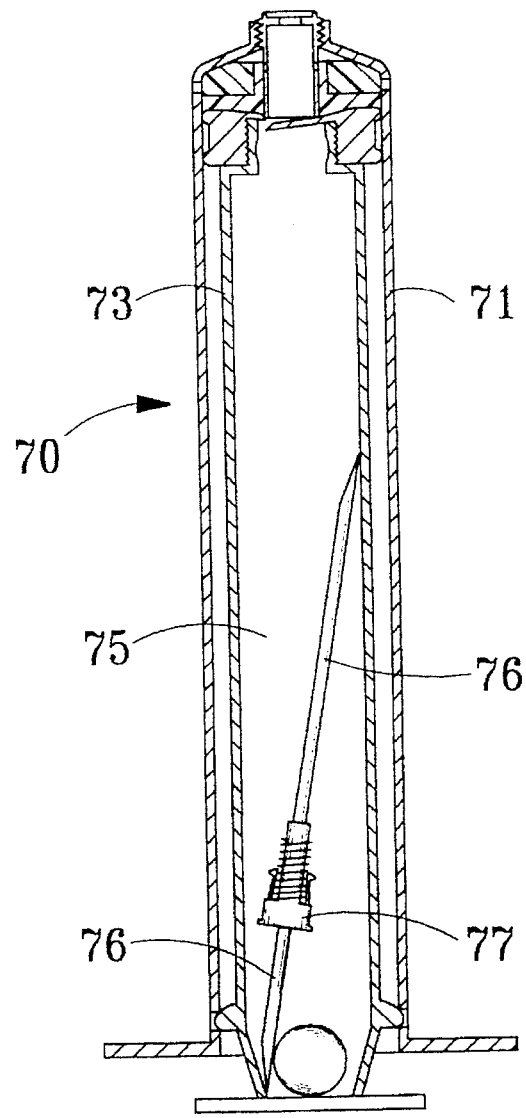
FIG. 12
FIG. 13

SAFETY INJECTOR WITH RETURNABLE NEEDLE

BACKGROUND OF THE PRESENT INVENTION

The present invention relates to a safety combined subcutaneous injector which is incorporated with needles of various dimension and returnable to an inner space of a hollow push rod of the injector.

A subcutaneous injector can be used for many purposes, for instance, by attaching a single head needle neck, it can be used for traditional subcutaneous hypodermic injection or intravenous injection to pour liquid medicine can also be applied to vacuum bloodletting by means of a double-pin headed subcutaneous injector needle to draw up the patient's blood into a vacuum tube.

The used injector needle must be broken or destroyed before it is abandoned. This can prevent the re-use of the contaminated needle and assure that the medicament and nursing personnel or junk cleaners will not be injured by the contaminated needle and accidentally infected by those mortal diseases as AIDS or hepatitis. The development of a safety injector which may get rid of the above mentioned fears and dangers is absolutely important.

The popular safety injector at present certainly can protect a third person from accidental injury by the injector's needle and prevent the acquiring of those infectious diseases. It is no doubt that the contribution of such injector is prominent. Its special feature in construction appears such a manner that the outer tube and the needle are made non-separable. In the other words, the outer tube dimension of a conventional injector and the size of the needle attached thereto is unchangeable. The kind and quantity of medicine to be injected, the position of injection on the patient body, and the dimension of the outer tube of the injector and its associated needle number should be predetermined. For example, an outer tube with a capacity of 5 cc may go with a needle elected from No. 1 to No. 14, and an outer tube with a capacity of 10 cc may also can be associated with a needle elected form No. 1 to No. 14 as well. Accordingly, there will be several hundreds of possible combination between the outer tubes and the needles that will puzzle the users of the injector during the selection of an appropriate injector to use. It is strongly hoped that the construction of the present safety injector may be as convenient as the traditional injector whose outer tube and the needle are separable so that the user can choose a free combination of the two components required.

In addition, there is a great difference in fundamental construction between the traditional injector, which can be used only once, and the safety injector as described above. The production equipment for the traditional injector will be no means available for making the safety injector without considerable renovations applied. This is not acceptable by an investor from the economic point of view.

SUMMARY OF THE PRESENT INVENTION

The main object of the present invention is to provide a safety injector whose needle is returnable to an inner space of a hollow push rod of the injector so as to avert the re-use of the contaminated needle by mistake and minimize the danger of injuring a third person. Moreover, the outer tube and needle of the safety injector may be freely combined and separated so that the hospital personnel can easily select the required sizes of the outer tube and needle to assemble an appropriate injector specified for the predetermined kind of medicine and quantity, the predetermined injecting location on the patient body. The present invention has the merits of not only convenient to handle but also reducing the production cost and minimizing the necessary amount of storage of injectors.

It is another object of the present invention to provide a safety injector which can be produced by automation with the conventional production equipment for the traditional injectors used for years without renovating the original equipment at large scale so that the manufacturer is able to maintain his commercial profits.

It is still another object of the present invention to provide a safety injector which is simple in construction, practical in application, easy for handling, and low in producing cost.

BRIEF DESCRIPTION OF THE DRAWINGS

The drawings disclose five illustrative embodiments of the present invention, which serve to exemplify the various advantages and objects hereof, as follows:

FIG. 12 is a cross sectional view of a joint usage of the safety injector according to the above second preferred embodiment of the present invention, which is associated with a blood collecting tube.

FIG. 13 is a longitudinal cross sectional view, showing the double pin head injector needle returning to the inner space of the hollow push rod of the safety injector, of the above second preferred embodiment of the present invention.

DETAILED DESCRIPTION OF THE PREFERRED EMBODIMENT

Figure 1:
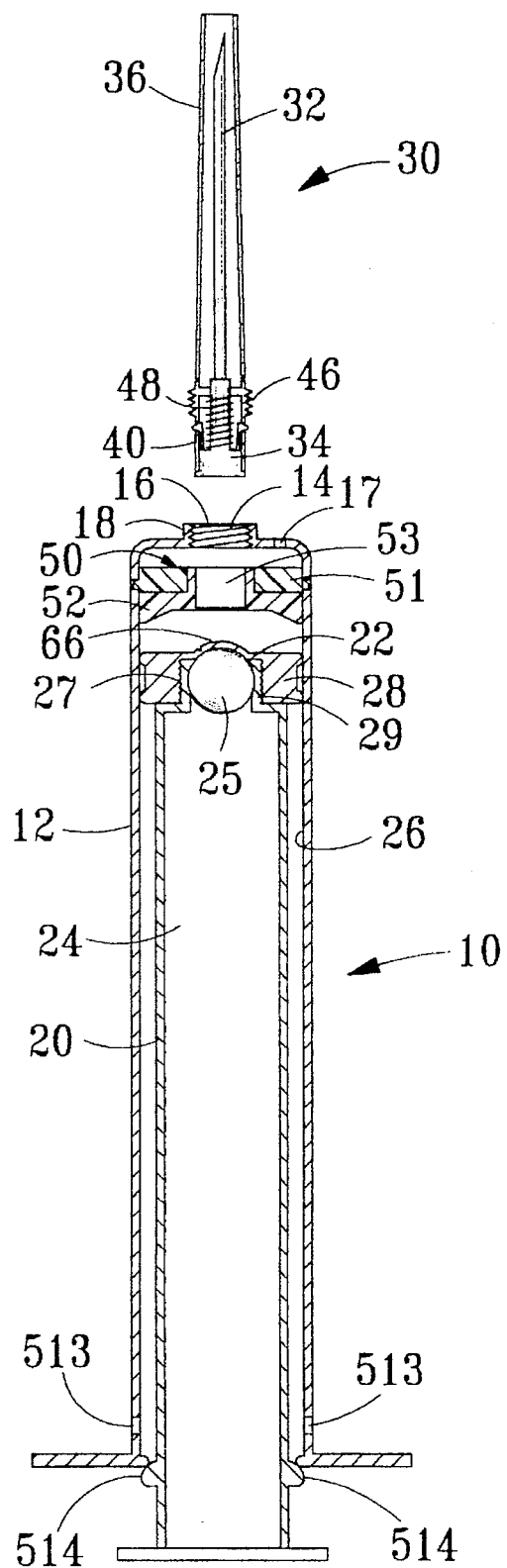
FIG. 1 is a longitudinal cross sectional view of a safety injector with returnable needle in its pre-assembled stage according to a first preferred embodiment of the present invention.
Figures 2, 3:
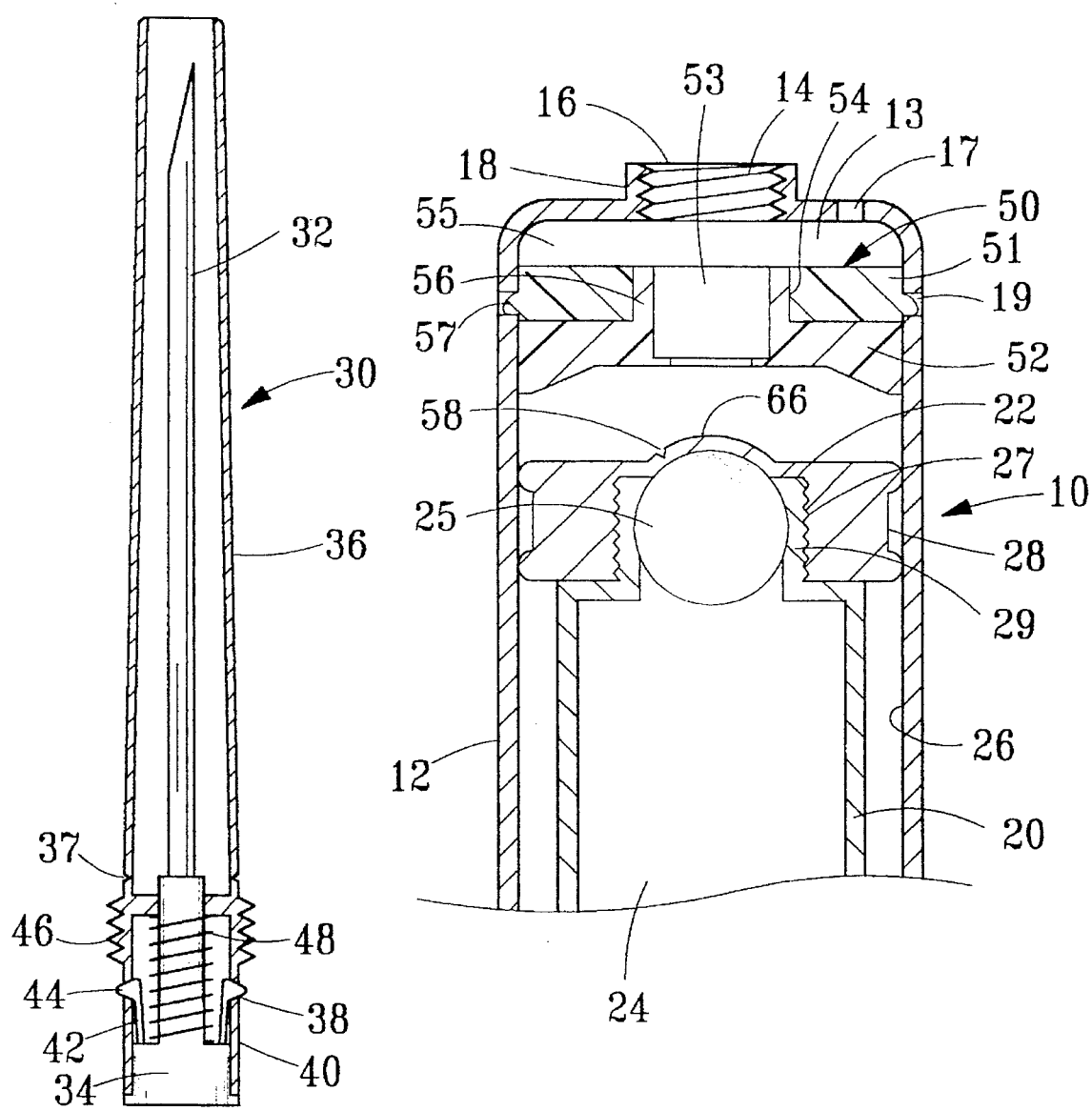
FIG. 2 is an enlarged cross sectional view of the injector needle assemblage of the safety injector as shown in FIG. 1.
FIG. 3 is an enlarged cross sectional view of the drug tube assemblage of the safety injector as shown in FIG. 1.

Referring to FIG. 1 and FIG. 3 simultaneously, it is observed that, in the first embodiment, a safety injector with returnable needle of the present invention comprises a drug tube assemblage 10, a injector needle assemblage 30, and a soft release element with fluid tight effect 50. The drug tube assemblage 10 comprises an outer tube for storing medicament 12. A top end of the outer tube 12 has an exhaust gas hole 17 and a hollow neck with an open mouth 16 extending therefrom. The hollow neck 18 has an inner screw threads 14 provided along an inner surface thereof. A top portion of the outer tube 10, below the exhaust gas hole 17, further has at least two symmetrically arranged position holding holes 19.

A hollow push rod 20 has an inner space 24 for receiving a molded injector needle 32 is slidably disposed in the outer tube 10. A top side of the push rod 20 extends a hollow neck 29 which has an open mouth 22 and an outer screw threads 27 extending along an outer surface thereof. A rubber plunger 28 is tightly screwed to the outer screw threads 27 on the top of the push rod 20 for simultaneous movement. The rubber plunger 28 contacts tightly with an inner wall surface 26 of the outer tube 12 to assure both fluid and vapor tight. The rubber plunger 28 comprises a frangible sealing element 66 which can be used to seal the open mouth 22 located on the top of the push rod. A spherule 25 is positioned on the tip of the inner space 24 for resisting pressure and averting the sealing element 66 which has a frangible surface 58 to be broken away by excessive pressure exerted before completion of injection.

The injector needle assemblage 30 comprises a body 40 with an outer threads 46, which can be either attached to the hollow 18 of the outer tube 10 by screwing or be freely separated from the outer tube 10 by unscrewing. The body 40 extends to reach a tubular needle cover 36 which is molded as one piece with the body 40. Between the needle cover 36 and the body 40, there is a frangible surface 37. The molded injection needle 32 is entirely positioned within the needle cover 36 with a part of the needle 32 extending into the body 40 to connect with a needle base 34 for supporting the needle 32. An elastic element 48 is positioned in the body 40 to exert a downwards force to the needle base 34. There are a pair of taper holes 38 formed on the body 40. The needle base 34 has a pair of catching claws 42 which extend upward and slightly outward. On a top of each catching claw 42 forms a taper flange 44 which is perpendicularly protruded outwards and is caught in the corresponding taper hole 38. When making the injector needle assemblage 30, the taper flange 44 of the catching claw 42 should precedingly hook onto the taper hole 38 of the body 40, and afterwards the injector needle 32 and its base 34 are fixed to the body 40 in a releasable manner.

A soft release element 50 comprises an upper piece 51 and a lower piece 52. In the middle of the upper piece 50, there is an open hole 54. The lower piece 52 has a central flange 56 which is firmly inlaid with the open hole 54 to form the release element 50. The release element 50 is set on the top of the outer tube 12, and at the same time a pair of jutting hooks 57 of the upper piece 51 is hooked on a pair of position holding holes 19 of the outer tube 12, so that the release element 50 and the outer tube 12 are closely fixed with each other to acquire a perfect fluid and vapor tight properties. There is a diminutive gap 55 remained between the upper piece 51 of the release element 50 and the top surface 13 of the outer tube 12. A center hole 53 is bred onto he lower piece 52 to properly accept the body 40.

Figures 4, 5:
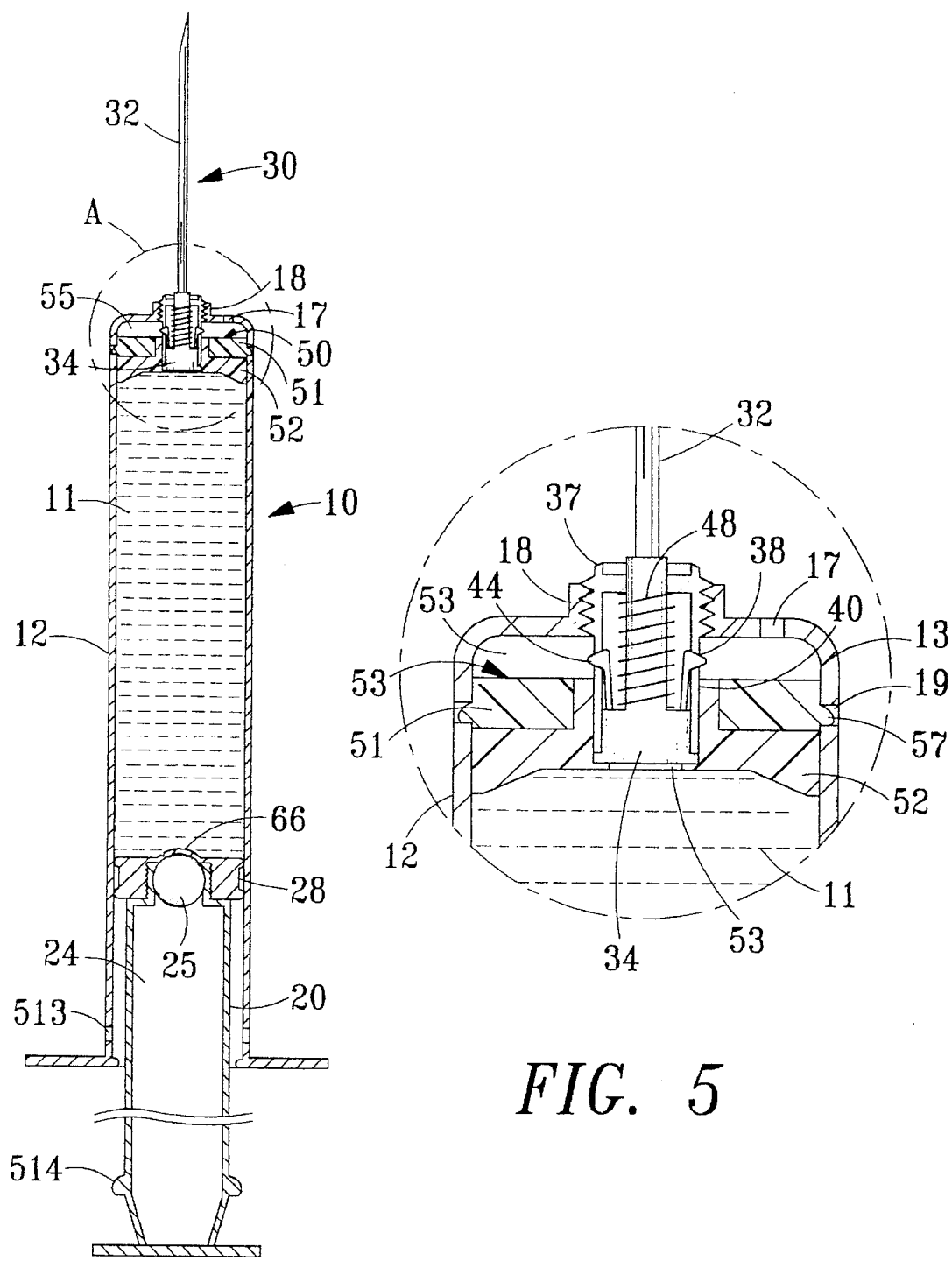
FIG. 4 is a longitudinal cross sectional view of the safety injector as shown in FIG. 1 on its position ready for injecting.
FIG. 5 is an enlarged view of Part in FIG. 4.

Referring to FIG. 4 and FIG. 5, the process of subcutaneous injection using the safety injector of the present invention is basically identical to that of using conventional injector. At first, select the injector needle assemblage 30 of appropriate dimension and screw it onto the neck 18 of the outer tube 12, at this moment, the lower half portion of the body 40 is firmly fixed to the center hole 53 of the soft release element 50 without loosing its fluid tight property. The taper flanges 44 and the taper holes 38, which are used for hooking on the needle base 34 and the body 40, just locate between the clearance 55 which is reserved between the soft release element 50 and the outer tube top surface 13. By maintaining this state, there is no worry of occurrence of separation between the needle base 34 and the body 40. After the assembly of the injector needle assemblage 30 and the drag tube assemblage 10 is accomplished, slightly twist the needle cover 36 and let it break along the frangible surface 37 and separate from the body 40, then the injector will be on its state ready for injecting as shown in FIG. 4. As the operator pulls backwards the push rod 20, the vacuum produced inside the outer tube will induce the fluid medicament 11 from a foreign container via the needle 32 into the inner space of the outer tube 12. Afterward, the fluid medicament 11 in the outer tube 12 can be injected outwards through the needle 32 by pushing the push rod 20 toward the needle 32.

Figures 6, 7:
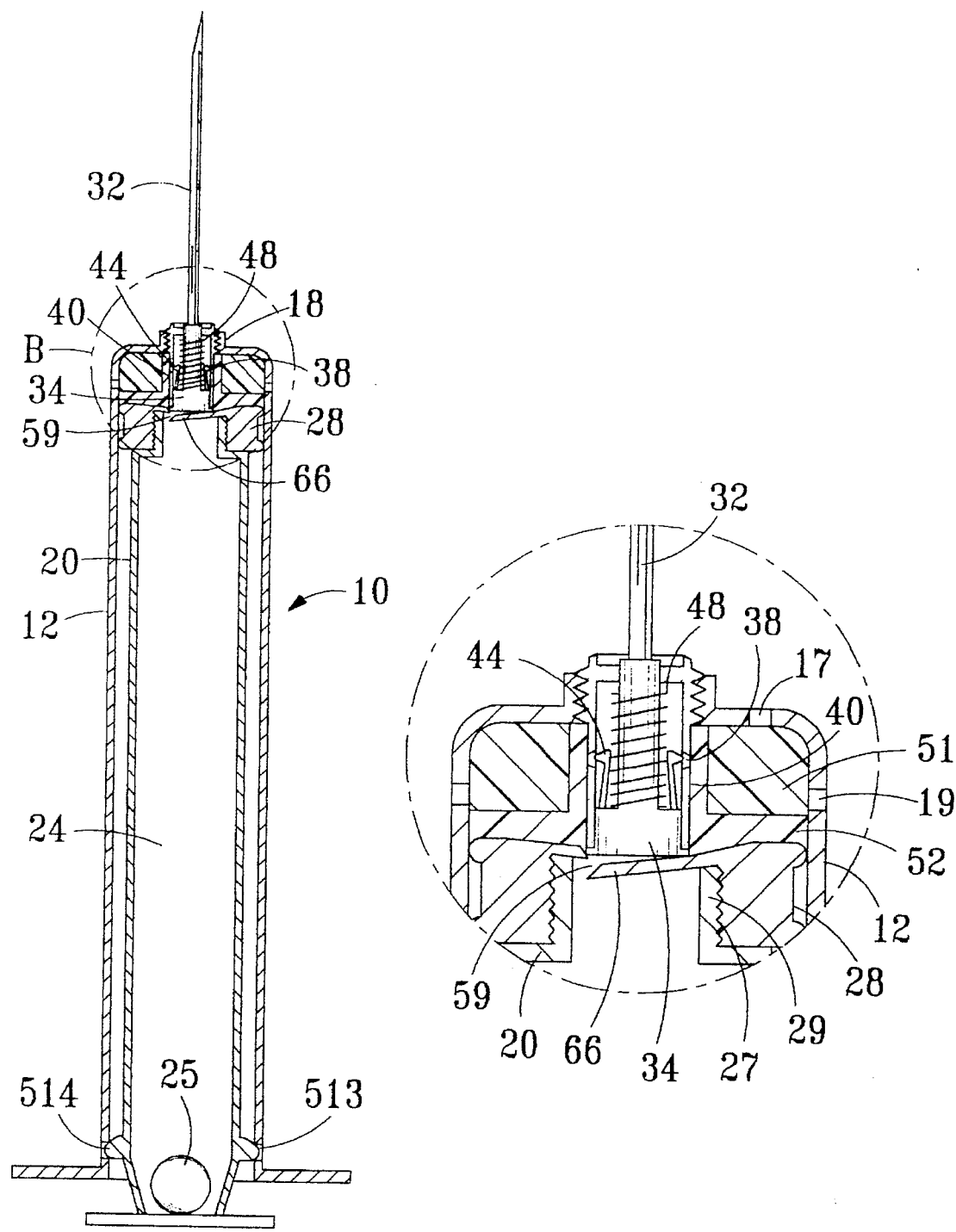
FIG. 6 is a longitudinal cross sectional view of the safety injector as shown in FIG. 4, after being finished injection, illustrating how the release element is forcing the needle base to separate from the body.
FIG. 7 is an enlarged view of part B in FIG. 6.
Figure 8:
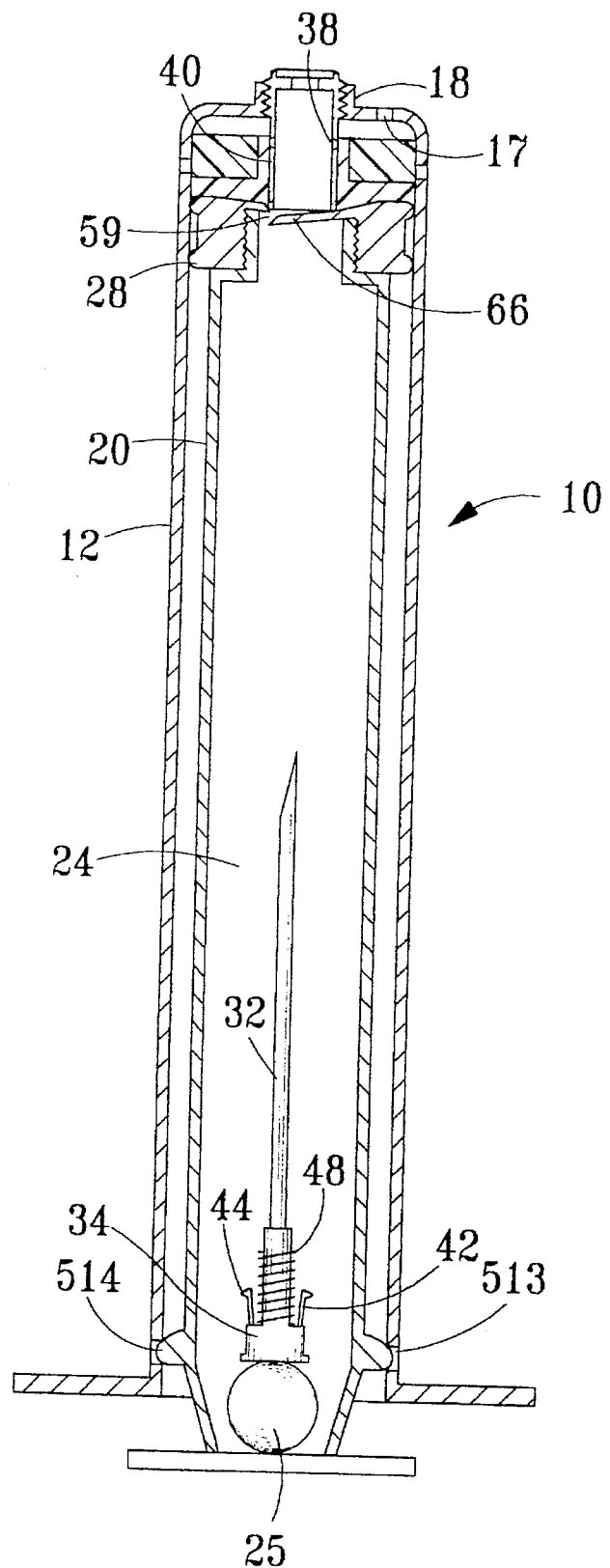
FIG. 8 is a longitudinal cross sectional view of the safety injector as shown in FIG. 4 with the needle and its base returning to the inner space of the hollow push rod.

Again referring to FIG. 6 and FIG. 8, after the injector has pushed out the medicament 11 stored in the inner space of the outer tube 12 entirely, the top surface of the rubber plunger 28 contacts the bottom surface of the lower piece 52 and the soft release element 50, the operator may go on pushing the hollow push rod 20 slightly until a pair of stopping flanges 514 located near a bottom end of the hollow push rod 20 inlay with a pair of stopping slots 513 near a bottom end of the outer tube 12. The function of the above mentioned mechanisms makes the hollow push rod 20 unable to be pulled out after completion of injection and averts the possibility of re-using contaminated injector. At the same time, as shown in FIG. 7 and FIG. 8, as the stopping flanges 514 of the push rod 20 inlay with the stopping slots 513 of the outer tube 12, a top 32 rim of the hollow push rod 20 is pushed up to the extent slightly higher or very nearly close to reach a bottom rim of the body 40 in order to cause the C-shaped frangible surface 58 (as shown on FIG. 9) on the sealing element 66 of the soft rubber plunger 28 to be squeezed by bottom rim of the fixed hard body 40 and form a pre-cracked open mouth 59. As soon as the open mouth 50 is formed, the C-shaped frangible surface 58 pushes the spherule 25 downwards into the inner space 24 of the hollow push rod 20, in which such space is originally prepared for accepting the injector needle. At the same time, the top rim of the hollow push rod 20 pushes the soft release element 50 upwards sot hat the pair of jutting hooks 57 are forced to separated form the pair of holding holes 19 of the outer tube 12 and move up. Being squeezed by the hard outer tube 12 and the body 40, the upwards moving of the soft release element 50 is partly squeezed into the taper holes 38, and furthermore the taper flanges 44 of the needle base will be pushed out of the taper holes 38 to release the needle base 34 from the body 40. At this moment, the injector needle 32 affixed on the needle base 34 is pushed by the elastic element 48 exclusively to move downwards, passes through the open mouth 59 formed by the pre-cracked C-shaped frangible surface 58 and jumps into the space 24 in the hollow push rod 20 above the spherule 25. Consequently, the injector needle is completely hidden without any exposed parts. With such mechanism no one may be injured by the contaminated injector needle accidentally, and that the re-use of the old needle will also be impossible.

Figures 9, 10:
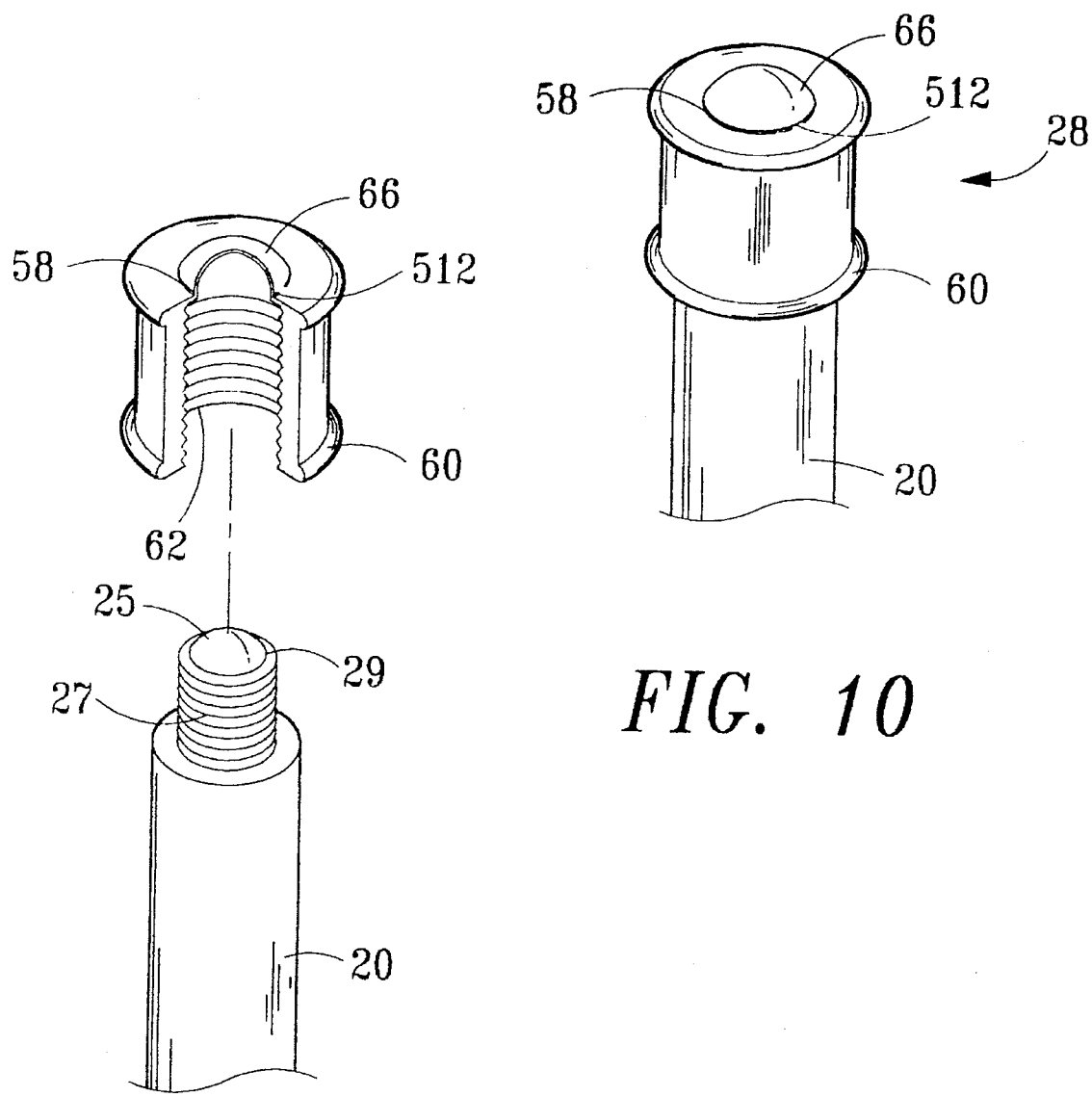
FIG. 9 is a three dimensional analytical drawing of the rubber plunger of the safety injector according to the above first preferred embodiment of the present invention.
FIG. 10 is a three dimensional view of the rubber plunger and the hollow push rod assembly according to the above first preferred embodiment of the present invention.

Referring to FIG. 7, FIG. 9 and FIG. 10, the above mentioned rubber plunger 28 is in cylinder shaped and the sealing element 66 provided in the middle of the top side of the rubber plunger 28 is in arc shape. Around the rim of the sealing element 66, there is the C-shaped frangible surface 58 and a very short connecting part 512. As mentioned in the above paragraph, after the injection has been accomplished, the C-shaped frangible surface is pressed and broken by the bottom rim of the body 40, and the sealing element 66 is connected to its rim merely with the short connecting part 512. As a result, when the needle base 34 is pushed down by the elastic element 48, the sealing element 66 can be pressed downwards and become perpendicular, and that the rubber plunger 28 forms the open mouth 59 admitting the needle base 34 and injector needle 32 to pass through. After the needle base 34 and the injector needle 32 being passed through the open mouth 59, the sealing element 66 will recover its approximately horizontal state by the elasticity of its own material to re-seal the mouth 59. The injector needle 32 and its base 34 occupying the inner space of the hollow push rod 20 can not come out through the open mouth 59 accidentally. The top and bottom sides of the rubber plunger 28 have two circular leak proof rings 60 respectively. The bottom of the plunger has an inner threads 62. When assembling, the inner threads 62 of the rubber plunger 28 are screwed with the outer threads 27 on the top side of the hollow push rod 20, and the circular leak proof rings 60 together with the inner wall surface 26 of the outer tube 12 can acquire fluid tight property. The push rod 20 and the rubber plunger 28 combine to move together. After having pushed out all the medicament contents in the outer tube and accomplished injection, the hollow push rod 20 may continue to move onwards to the position as shown in FIG. 7.

Figure 11:
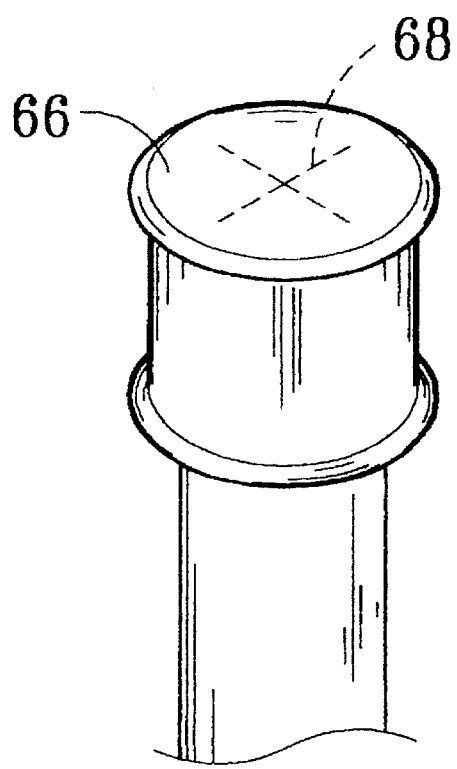
FIG. 11 is a three dimensional view of the rubber plunger and the hollow push rod assembly of a safety injector according to a second preferred embodiment of the present invention.

Referring to FIG. 11, this is a second preferred embodiment related to the rubber plunger. The C-shaped frangible surface surrounding the sealing element 66 as disclosed in the above first embodiment can be directly replaced by the cross type shallow slot 68 equipped at the bottom of the sealing element 66. This cross type shallow slot 68, being not yet punched through, still possess the fluid tight effect when the injection is proceeding, and can prevent the medicament form intruding into the space for accepting the injection needle. After completion of injection, the cross type shallow slot 68 is cracked to form an open mouth owing to the pressure imposed by the body 40, so that both the needle base and the needle can enter the inner space of the inner tube via the open mouth.

Referring to FIG. 12 and FIG. 13, the injector needle extending only in one single direction from the needle base, as described in the first embodiment of the present invention as shown in FIG. 1, can be altered to extend in dual-direction, i.e. upwards and downwards respectively from the injector needle base 77 forming a double point head injector needle 76 in the second embodiment as shown in FIG. 12. This can be utilized in the field of hematological examination in co-operation with the conventional blood collecting tube. The safety injector in the second embodiment comprises a drug tube assemblage 70 which is entirely identical to that employed in the first embodiment, a soft release element 72 and an injector needle assemblage 74 which is identical to that employed in the first embodiment, except that a double point head needle 76 is utilized instead. As shown in FIG. 12, the handling method of the safety injector in the second embodiment is described as follows. At first, pull the hollow push rod 73 of the drug tube assemblage 70 completely out of the outer tube 71. Next, insert the blood collecting tube 78 with the sealing piece 79 on top of it into the inner part of the outer tube 71, and penetrate through the sealing piece 79 with the bottom ping head of the double point head injector needle 76. The hematological examination by traditional method can be operated hereafter. Referring to FIG. 13, after finishing the operation, insert again the hollow push rod 73 into the outer tube 71, and go on pushing the hollow push rod 73 in upwards direction as it is done in the first embodiment. The double point head injector needle 76 will be put inside the injector needle accepting space 75 in the hollow push rod 73.

Figure 14:
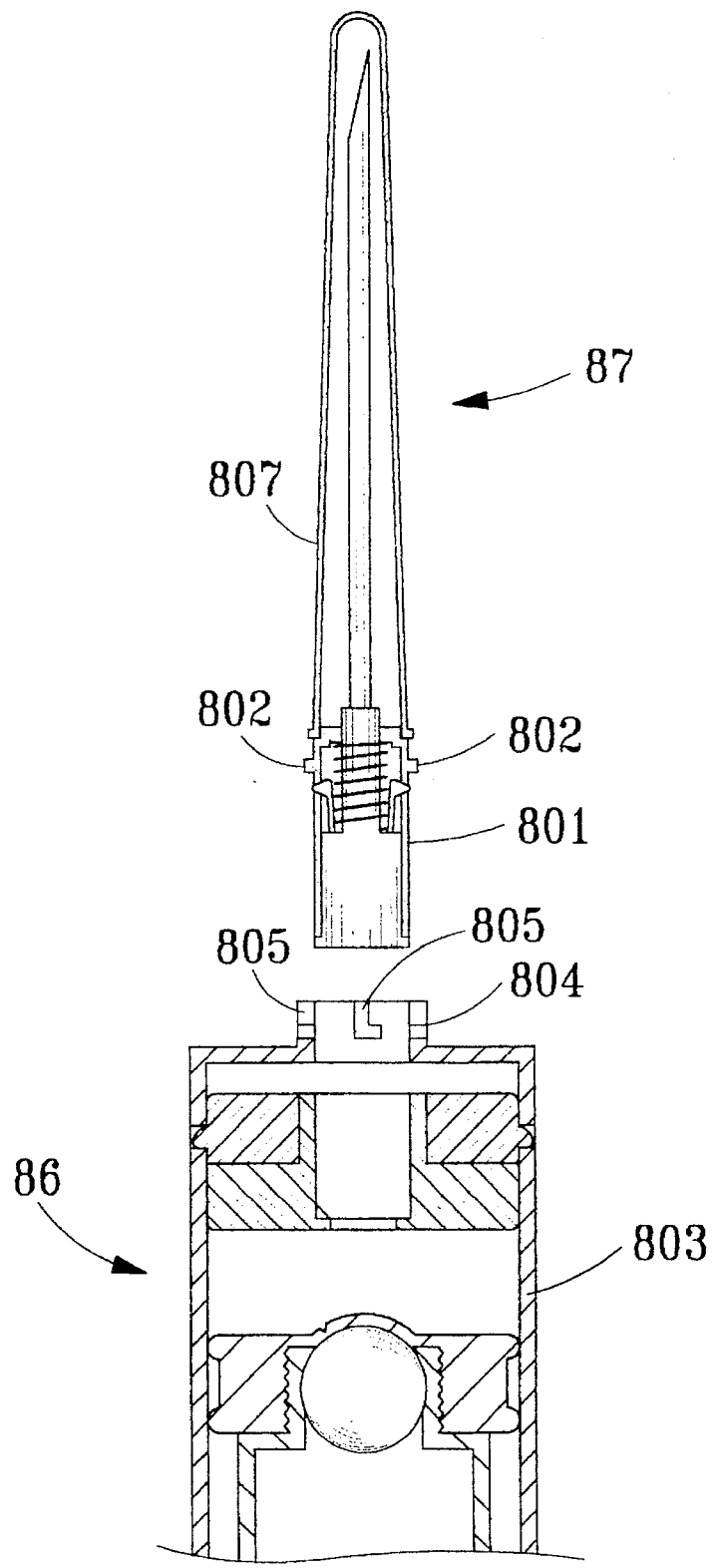
FIG. 14 is an enlarged cross sectional view a safety injector with returnable needle in its pre-assembled stage according to a third preferred embodiment of the present invention.

Referring to FIG. 14, the main construction of a safety injector in a third embodiment is essentially identical to that in the first embodiment. The main differences with the former is described as follows. The body 801 in the injector needle assemblage 87 has several hook flanges 802. On the neck 804 of the outer tube 803, there are several L-shaped conducting slots 805 for inlaying with the hook flanges 802 mutually. Consequently, the injector needle assemblage 87 and the drug tube assemblage 86 may be mutually fixed with each other in replaceable way by means of the hook flanges 802 and L-shaped conduction slots 805. In addition, the needle cover 807 and the body 801 are two independent pieces which can be separated or attached with each other that this is different from those molded in one unseparated piece as in the first embodiment.

Figures 15, 16:
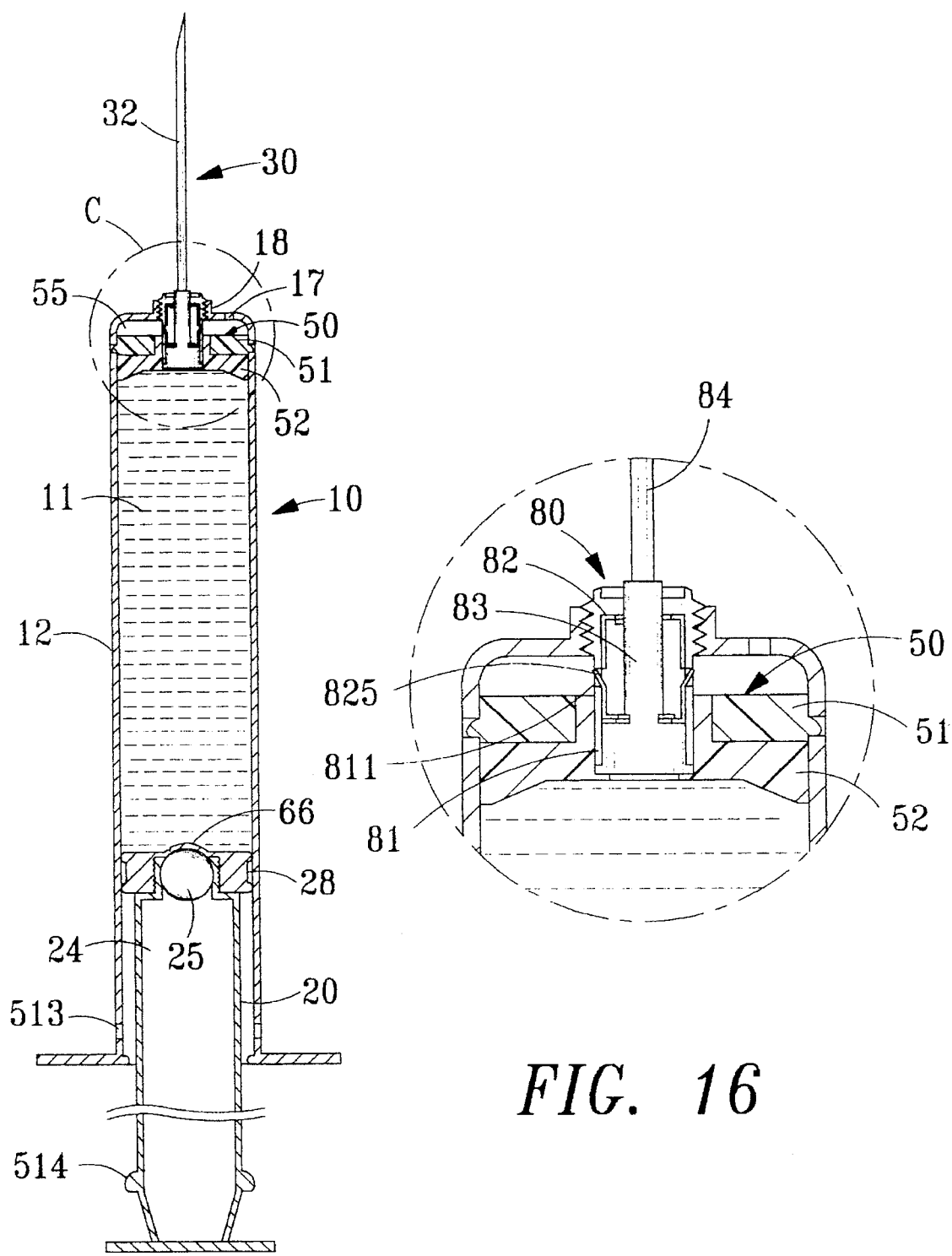
FIG. 15 is a longitudinal cross sectional view of a safety injector with returnable needle in a position ready for use according to a fourth preferred embodiment of the present invention.
FIG. 16 is an enlarged C portion cross sectional view of the injector needle assemblage of the safety injector as shown in FIG. 15.
Figure 17:
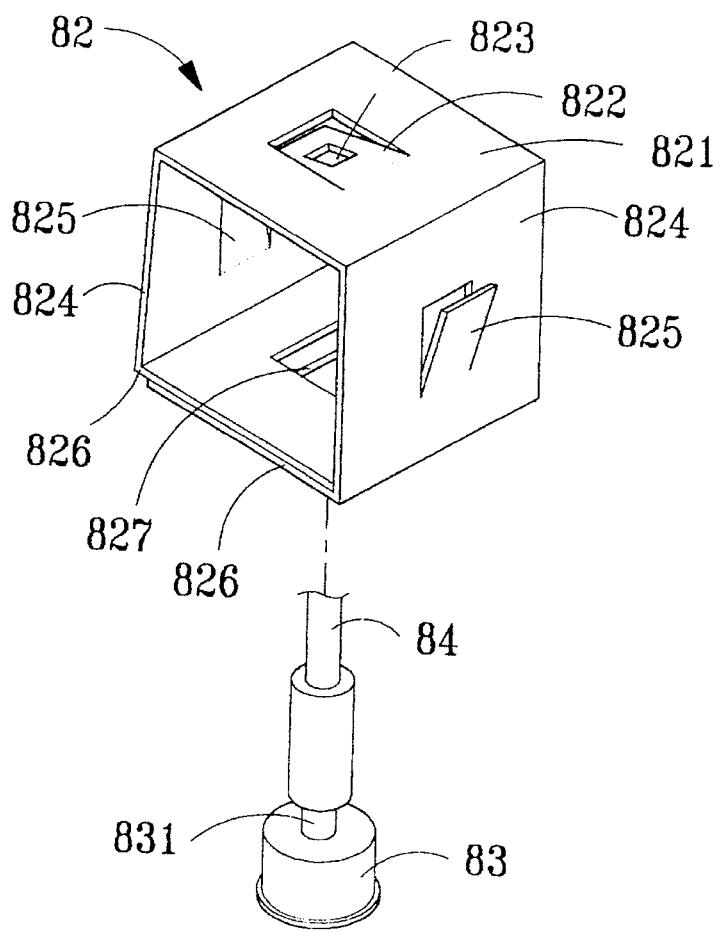
FIG. 17 is an analytic drawing of the wedged supporting base with wedged needle base according to the above preferred fourth embodiment of the present invention.
Figure 18:
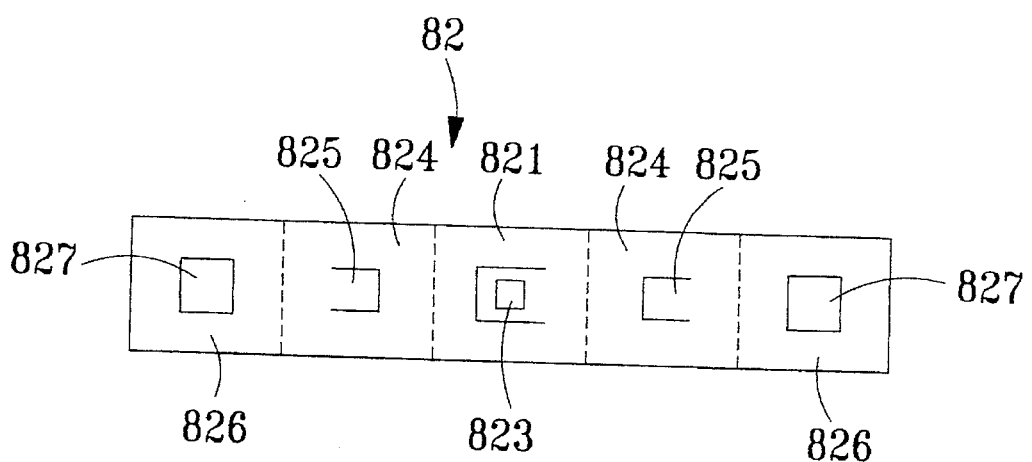
FIG. 18 is a developed drawing of the wedged supporting base according to the above preferred fourth embodiment of the present invention.

Referring to FIG. 15, FIG. 16. FIG. 17, and FIG. 18, the main construction of a safety injector in a fourth embodiment is essentially identical to that in the first embodiment. The main differences with the former embodiments are described as follows. A wedge holding base for the wedging needle base 83 is utilized to replace the taper flange 44 and elastic element 48 in the former embodiments. The holding base 82 is made of a plane material which shows in long narrow shape if developed. As shown in FIGS. 17 and 18, the middle position of the plane material contribute a top portion 821, on which there is an inversely U-shaped elastic piece 822. On the elastic piece 822, there is a hole 823 formed. Both sides of the top portion 821 are each connected to a side wall 824, on which there is a hook on piece 825 formed. Each hook on piece 823 is shaped by pressing in the outwards direction. Each side wall 824 is further connected to a bottom base 826 on which there is a gripping hole 827 formed. The plane material can turn the holding base 82 into a square shape by folding along the dotted lines as shown in FIG. 18. When assembling the holding base 82 in the body 81, its hook on piece 825 is at first hooked on to the hooking hole 811 of the body 81. Then assemble the injector needle assemblage 80 in the wedge holding base 82, so that its gripping hole 827 can be gripped on a gripping slot 831 provided on the needle base 83, and that the injector needle 84 and its base 83 are gripped firmly on the holding base 82 in releasable manner.

Figures 19, 20:
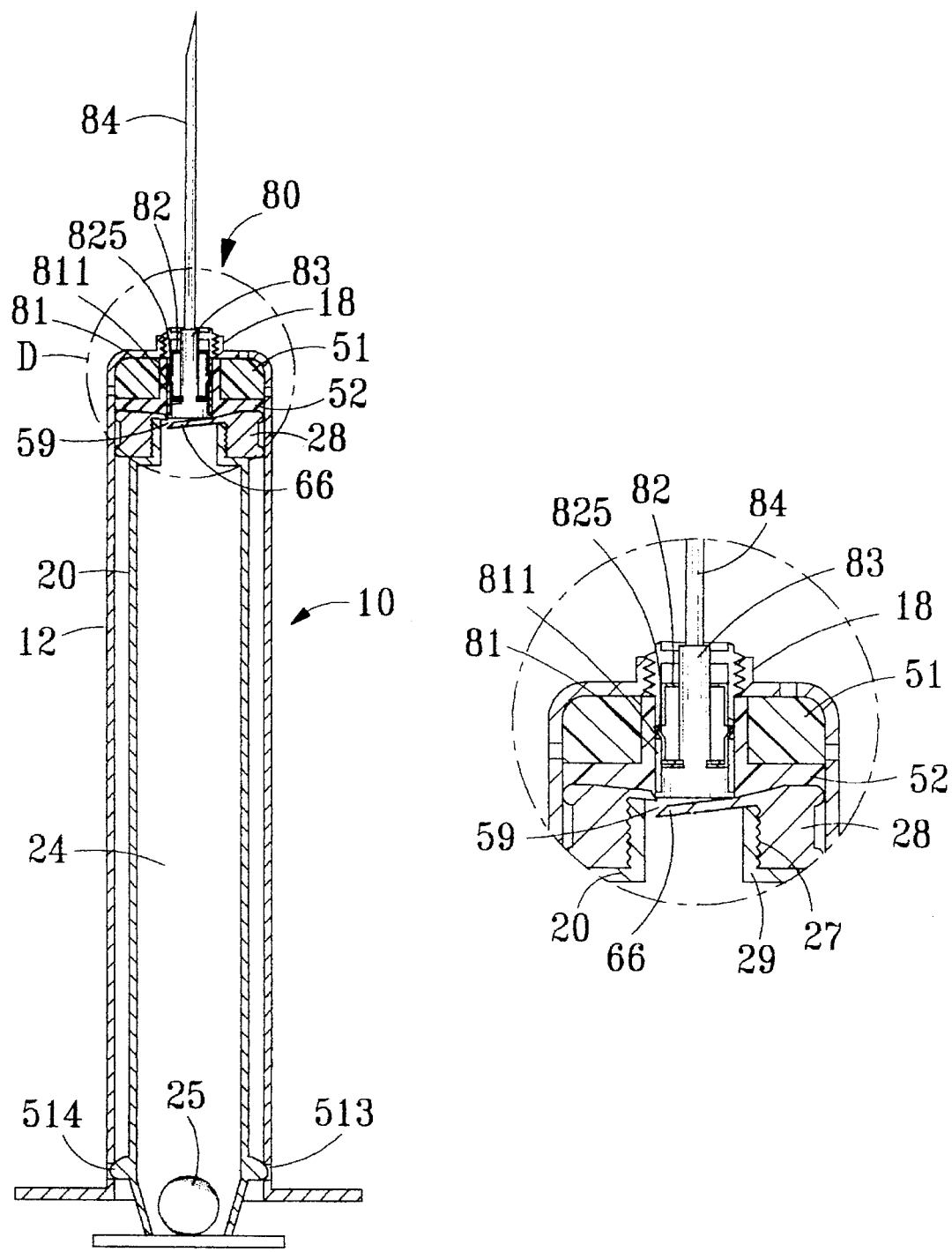
FIG. 19 is a longitudinal cross sectional view of the safety injector with returnable needle of the present invention in the state after accomplishing injection.
FIG. 20 is an enlarged drawing of D portion as shown in FIG. 19.

Referring to FIG. 19 and FIG. 20, when the soft release element 50 on its way upwards is oppressed by the hared outer tube 12 and the body 81, it is partly squeezed into the hooking hold 811 on the body 81. Furthermore, the hook on piece 825 of the needle base 83 is squeezed out of the hooking hole 811 so that the mutual gripping between the needle base 83 and the holding base 82 will be released. At this time, the injector needle 84 originally fixed on the needle base 83 will displace downwards and pass through the open mouth 59 on the sealing element 66 which has been formed by pre-cracked C-shaped frangible surface 58 and drops into the inner space 24, which is originally prepared for the needle 84, of the hollow push rod 20 above the spherule 25. In this way, the injector 84 is entirely concealed without exposing any portion outside. The danger of injuring anybody by used needle or to re-use of the contaminated needle will be absolutely avoided.

Figures 21, 22:
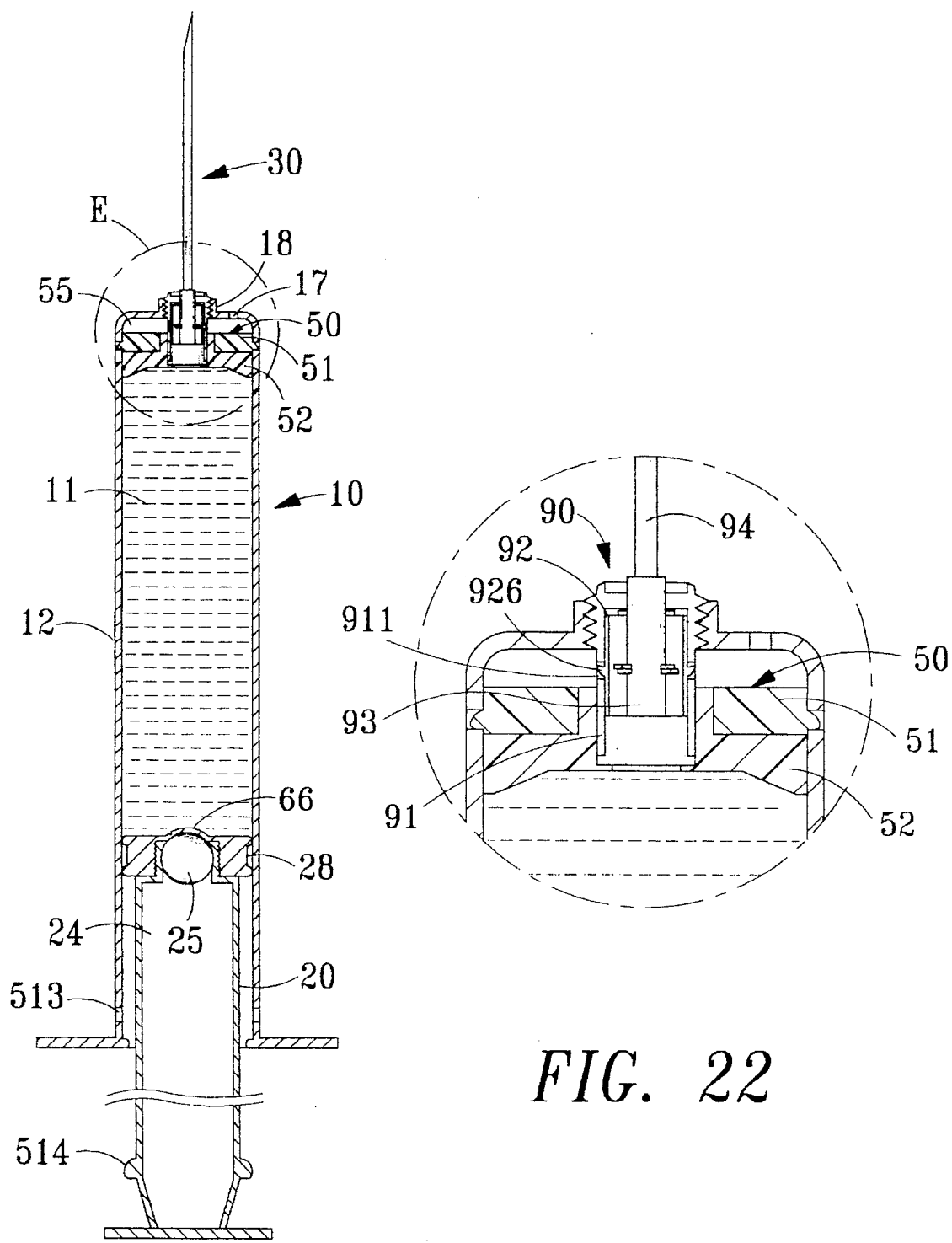
FIG. 21 is a longitudinal cross sectional view of a safety injector with returnable needle in a position ready for use according to a fifth preferred embodiment of the present invention.
FIG. 22 is an enlarged drawing of E portion as shown in FIG. 21.
Figure 23:
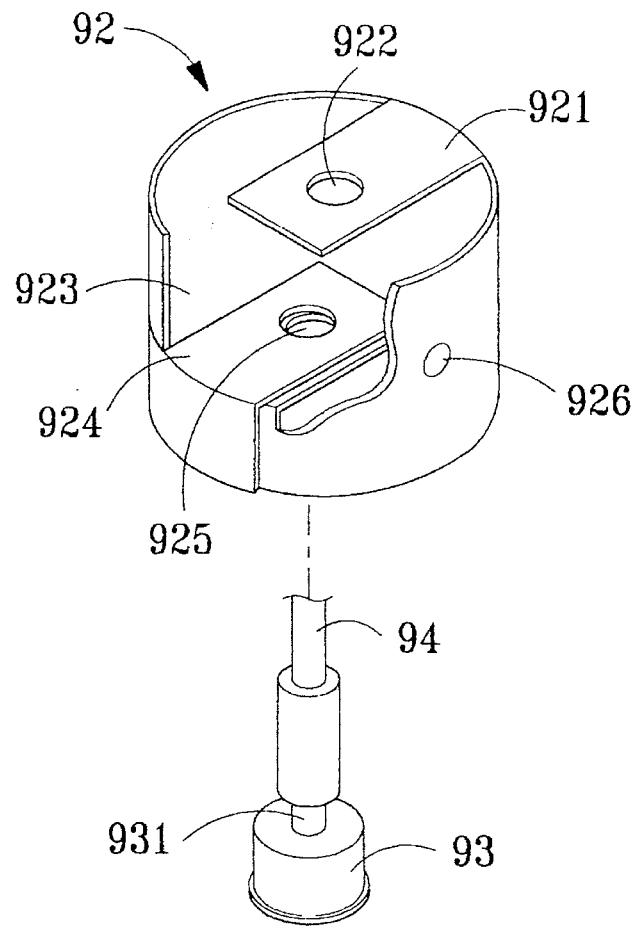
FIG. 23 is an analytical drawing of the wedged supporting base and wedged needle base according to the above fifth preferred embodiment of the present invention.
Figure 24:
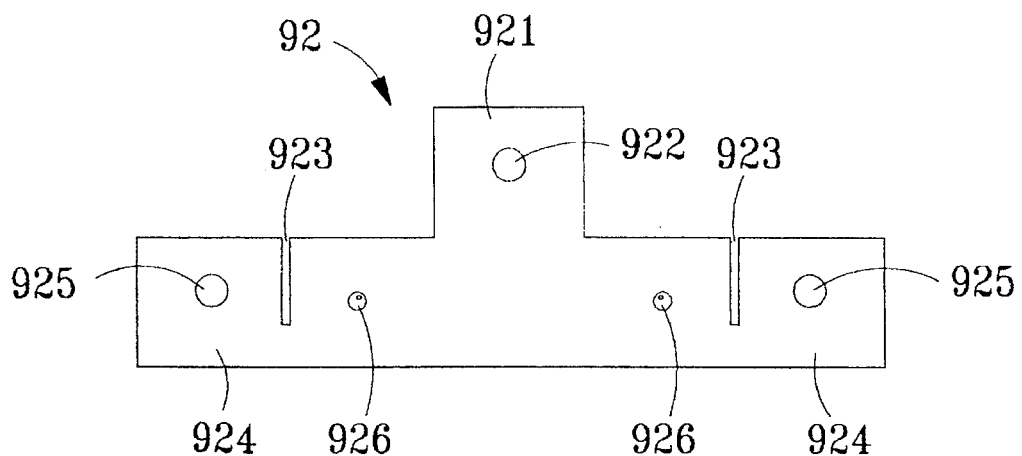
FIG. 24 is a developed drawing of the wedged supporting base according to the above fifth embodiment of the present invention.

Referring to FIG. 21, FIG. 22 and FIG. 23, the main construction of a safety injector in a fifth embodiment provided by the present invention is essentially identical to that in the first embodiment. The main differences with the former embodiments are described as follows. In the body 91 of the injector needle assemblage 90, there is a holding base 92 which can catch in the needle base 93. The holding base 92 is made of a plane material into an inversely T-shaped figure (as shown in FIG. 24) which has a middle portion and two wings transversely extending from the middle portion. An elastic cover 921 which has a central gripping hole 922 formed thereon is running upwards from the middle portion of the plane material. Each wing of the T-shaped plane material provides a slot 923 in its middle portion, a gripping piece 924 at its end portion and a hook on piece 926 protruded between the middle portion 921 and the slot 923. On each gripping piece 924, there is a gripping hole 925 so that the plane material can be assembled in a barrel figure. The two gripping pieces 924 overlap with each other and are folded down along the slots 923 respectively to maintain horizontal. The two gripping holes 925 also overlap with each other. On assembling the holding base 92 in the body 91, the two hook on pieces 926 should be hooked to the hooking holes 911 formed on the body 91 in advance before assembling the injector needle assemblage 90 in the holding base 92, so that the gripping hole 922 on the holding base 92 may grip on a gripping slot 931 provided on the needle base 93. Then, the injector needle 94 and its needle base 93 may be gripped firmly on the holding base 92 with releasable manner.

Figures 25, 26:
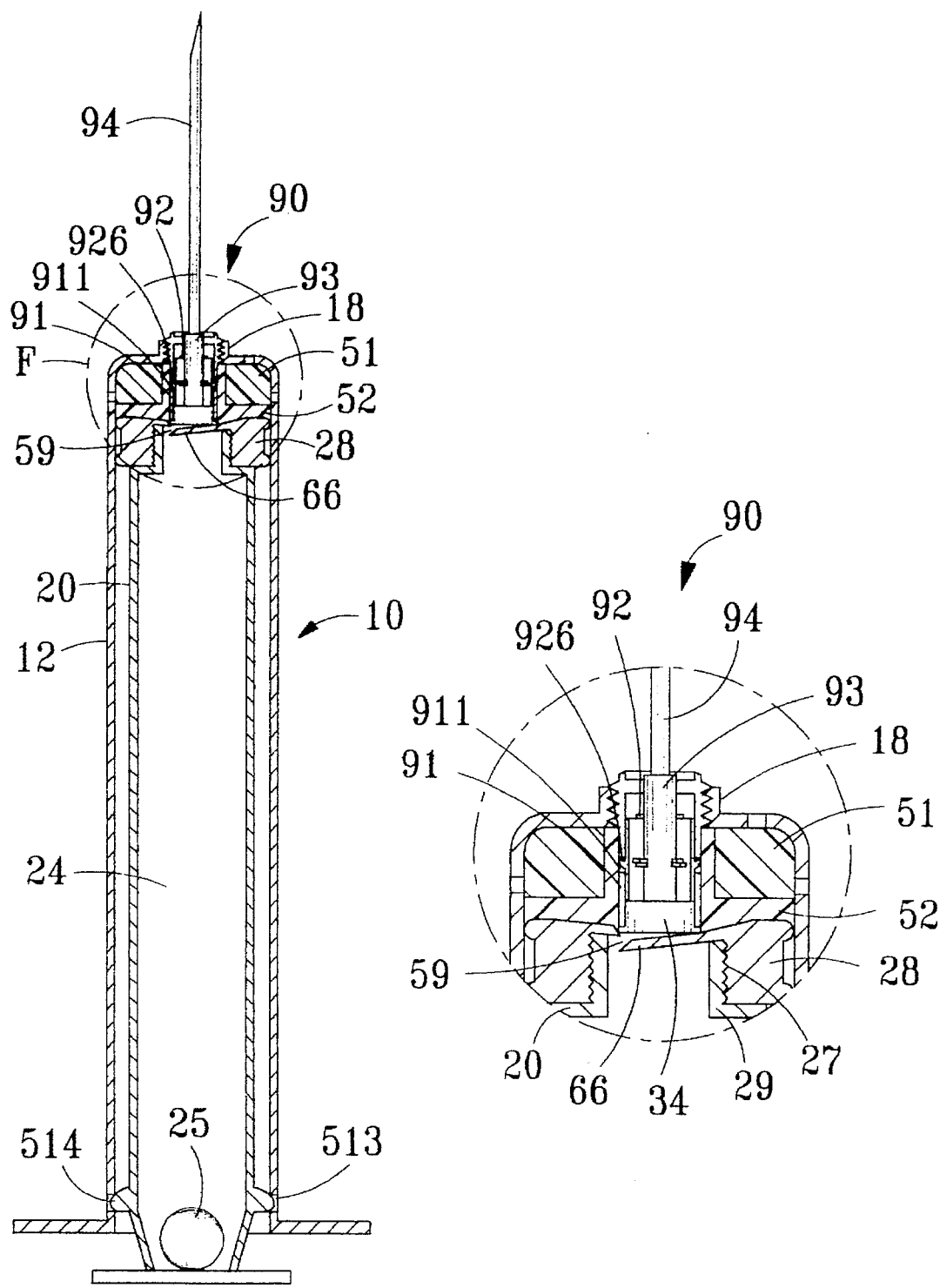
FIG. 25 is a longitudinal cross sectional view of the safety injector with returnable needle of the present invention in the state after accomplishing injection.
FIG. 26 is an enlarged drawing off portion as shown in FIG. 25.

Referring to FIG. 25 and FIG. 26, when the soft release element 50 on its way upwards is oppressed by the hard outer tube 12 and the body 91 and is partly squeezed into the hooking hole 911 on the body 91, the hook on piece 926 of the needle base 93 is squeezed out of the hooking hole 911, so that the mutual gripping between the needle base 94 and the holding base 92 will be released. At this time, the injector needle 94 originally affixed on the needle base 93 will displace downwards and pass through the open mouth 59 on the sealing element 66 which has been formed by pre-cracked C-shaped frangible surface 58 and drops into the inner space 24, which is originally prepared for the needle 94, of the hollow push rod 20 above the spherule 25. In this way, the injector needle 32 is entirely concealed without exposing any portion outside. The danger of injuring anybody by used needle or to re-use of the contaminated needle will be absolutely avoided.

The safety injector of the present invention provides an interior enclosing space for the needle, after injection, the needle will be in that space entirely by successive motions of the components of the injector assembly. This leads to minimize the possibilities of injuring the third person by using needle accidentally and avoid the re-use of the contaminated needle by carelessness as well. Moreover, the outer tube and needle of the injector may be freely combined and separated so that the hospital personnel can easily select the combination of the predetermined outer tube size and needle number for specified kind of medicine and quantity and specified injection location on the patient body. It has the merits of not only convenient to handle but also reducing the production cost and minimizing the necessary amount of storage of injectors.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

I claim:

1. A safety injector, comprising
   a drug tube assemblage which comprises an outer tube for storing medicament, a hollow push rod which has an open mouth on a top thereof and an inner space therein, and a rubber plunger affixed to said top of said push rod for maintaining fluid tight properly with said outer tube and enabling said push rod and said rubber plunger to move together while injecting, in which said outer tube has an exhaust gas hole formed on a top thereof and a hollow neck extended from said exhaust gas hole, said rubber plunger including a sealing element which has a frangible surface for sealing said open mouth provided on said top of said hollow push rod, so that after the medicament in said outer tube has entirely been injected, the motion of said rubber plunger is braked up and a relative motion occurred between said rubber plunger and a continuously movement of said push rod forces said frangible surface of said sealing element to crack due to a squeezing effect by said relative motion, said drug tube assemblage further comprising a spherule positioned on a top of said inner space for resisting pressure and preventing said frangible sealing element to crack by any excessive pressure before the medicament has not been injected; and an injector needle assemblage, which is replaceably connected and affixed to said drug tube assemblage, comprising a body connected and affixed to a top side of said hollow of said outer tube in such a manner that said body is capable of separating again from said hollow neck of said outer tube when it is necessary, an injector needle extended out of said body, a needle base which is temporary hooked to an inner part of said body in a releasable manner and is molded in one piece with said injector needle for supporting said injector needle, at least an elastic element which is positioned in said body for exerting downwards an elastic force to said needle base, a soft release element having an upper piece and a lower piece for preventing the medicament intruding in said body, said soft release being positioned in a top portion of said outer tube for maintaining a fluid tight property with an inner surface of said outer tube, thereby after the medicament is injected up by a pushing force exerted by said rubber plunger which is moved together with said push rod, said soft release element being pushed to move for a very short distance by said push rod so as to separate said needle base form said body and provide a squeezing force to exert said elastic element, said needle base and said injector needle being slipped into said inner space of said push rod after passing through said pre-cracked frangible surface of said sealing element.

2. A safety injector, as recited in claim 1, in which at least two taper holding holes are provided on said body, and that at least two hook on pieces extending upwards and slightly outwards from said needle base, wherein each of said hook on pieces has a taper flange formed on a top side thereof and extended perpendicularly and outwardly for pre-hooking to said corresponding taper holding hole, thereby after the medicament has been entirely injected up, said taper flanges being separated from said taper holding holes by said squeezing force from said soft release element which is pushed by said push rod.

3. A safety injector, as recited in claim 1, in which a pair of hook on pieces are extended upwards and slightly outwards from said needle base, wherein each of said hook on pieces formed a taper flanges on a top side thereof and extended perpendicularly outwards, and that a pair of taper holding holes are provided on said body for pre-hooking with said pair of hook on pieces respectively, thereby after the medicament has been entirely injected up, said taper flanges being separated from said taper holding holes by said squeezing force from said soft release element pushed by said push rod.

4. A safety injector, as recited in claim 1, in which said hollow neck of said outer tube and said body provide a plurality screw threads respectively, and that said screw threads of said neck and said body are match with each other by screwing.

5. A safety injector, as recited in claim 1, in which said neck of said outer tube has a plurality of conducting slots provided thereon and said body has a plurality of flanges provided thereon for inlaying with said conducting slots respectively.

6. A safety injector, as recited in claim 1, in which said injector needle has two point heads extending upwards and downwards from said needle base respectively.

7. A safety injector, as recited in claim 1, in which said rubber plunger further has two parallel arc-shaped jutting leakage proof and fluid tight pieces are formed on an upper side and a lower side thereof for ensuring tightly close contact with said outer tube.

8. A safety injector, as recited in claim 1, in which an inner surface of said rubber plunger has an inner screw threads and an outer surface of said top of said push rod has an outer screw threads, so that said rubber plunger is screwed onto said push rod.

9. A safety injector, as recited in claim 1, in which said frangible surface of said sealing elements is in C-shaped.

10. A safety injector, as recited in claim 1, in which said frangible surface of said sealing element is an incomplete cross shaped shallow slot which is easy to crack while exerting by a force.

11. A safety injector, as recited in claim 1, in which said body of said injector needle assemblage further comprises a square shaped needle holding base positioning in said body and being folded from a plane material which is formed in a long narrow shape comprising a middle position which has an inversely U-shaped elastic piece with a hole formed thereon, and that each side of said middle position is perpendicularly connected to a side wall which provides a hook on piece formed by pressing in outwards direction on said side wall for hooking with a pair of hooking holes provided on said body, and that each of said side walls further perpendicularly connects a bottom base with a gripping hole thereon, wherein said two bottom base and said gripping holes thereon are overlapped for gripping said needle base in position.

12. A safety injector, as recited in claim 1, in which said body of said injector needle assemblage further comprises a holding base positioning in said body and being folded from a plane material to form an inversely T-shaped figure which has a middle portion and two wings transversely extending from two sides of said middle portion, and that an elastic cover which has a central gripping hole formed thereon is running upwards from said middle portion, and that each of said wings provides a slot in its middle position, a gripping piece at its end portion which has a gripping hole formed thereon and a hook on piece protruded between said middle portion and said slot for hooking with a pair of hooking holes provided on said body, wherein said two gripping pieces are overlapped with each other and folded down along said two slots respectively to maintain horizontal, and that said two gripping holes are also overlapped with each other for firmly gripping with said needle base.

* * * * *